US012721557B2

(12) United States Patent
Salehi Borojerdi et al.

(10) Patent No.: US 12,721,557 B2
(45) Date of Patent: Sep. 1, 2026

(54) OVERMOLDED HEMOLYSIS-REDUCTION ACCESSORIES FOR DIRECT BLOOD DRAW

(71) Applicant: CareFusion 303, Inc., San Diego, CA (US)

(72) Inventors: Alireza Salehi Borojerdi, Aliso Viejo, CA (US); Amarsinh Deeliprao Jadhav, Bangalore (IN); Mohammed Mehtab Khan, Bengaluru (IN); Shelby Ann Bieritz, Durham, NC (US); Chris Jesse Zollinger, Chino, CA (US); Ryan Schoonmaker, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 562 days.

(21) Appl. No.: 18/187,215

(22) Filed: Mar. 21, 2023

(65) Prior Publication Data

US 2023/0309872 A1 Oct. 5, 2023

Related U.S. Application Data

(60) Provisional application No. 63/326,705, filed on Apr. 1, 2022.

(51) Int. Cl.
*A61B 5/15* (2006.01)
*A61M 25/00* (2006.01)

(52) U.S. Cl.
CPC .... *A61B 5/15003* (2013.01); *A61B 5/150221* (2013.01); *A61M 25/0097* (2013.01)

(58) Field of Classification Search
CPC ....................... A61B 5/15003; A61M 25/0097
See application file for complete search history.

(56) References Cited

U.S. PATENT DOCUMENTS 3,893,892 A * 7/1975 Mehl ................ A61B 5/150099 600/577
5,409,477 A 4/1995 Caron et al.
2005/0059958 A1 * 3/2005 Lessard ............ A61M 25/0009 604/533
2006/0264904 A1 * 11/2006 Kerby ............... A61M 25/0043 604/523

(Continued)

FOREIGN PATENT DOCUMENTS

EP 0160807 A2 11/1985
EP 1800598 A1 6/2007

(Continued)

OTHER PUBLICATIONS

International Search Report and Written Opinion for Application No. PCT/US2023/015017, dated Jun. 23, 2023, 15 pages.

(Continued)

*Primary Examiner* — Daniel L Cerioni
(74) *Attorney, Agent, or Firm* — MASCHOFF BRENNAN

(57) ABSTRACT

A flow restriction device may include a male luer connector portion, a female luer connector portion, a tube, and an overmolded body portion. The male luer connector portion defies a first lumen. The female luer connector portion defines a second lumen. The tube defines a third lumen. The third lumen is in fluid communication with the first lumen and the second lumen. The third lumen has a diameter less than 0.025 inches. The overmolded body portion is formed around the tube.

15 Claims, 4 Drawing Sheets

(56) References Cited

U.S. PATENT DOCUMENTS

| | | | | |
|---|---|---|---|---|
| 2012/0277627 | A1 | 11/2012 | Devgon | |
| 2013/0304037 | A1* | 11/2013 | Fangrow | A61M 39/1011 604/535 |
| 2015/0011929 | A1* | 1/2015 | Dawood | A61B 90/70 604/22 |
| 2021/0046301 | A1* | 2/2021 | Fangrow | A61M 39/26 |
| 2021/0137436 | A1 | 5/2021 | Burkholz et al. | |
| 2021/0228127 | A1 | 7/2021 | Burkholz et al. | |
| 2022/0047195 | A1 | 2/2022 | Ma et al. | |
| 2022/0176079 | A1* | 6/2022 | Cook | A61B 5/153 |
| 2022/0330858 | A1* | 10/2022 | Thompson | A61B 5/15003 |

FOREIGN PATENT DOCUMENTS

| | | | |
|---|---|---|---|
| JP | S6137171 | A | 2/1986 |
| JP | 2003500122 | A | 1/2003 |
| WO | 0071196 | A1 | 11/2000 |
| WO | WO-2006052655 | A2 | 5/2006 |

OTHER PUBLICATIONS

International Preliminary Report on Patentability from the International Preliminary Examining Authority for Application No. PCT/US2023/015017, dated Mar. 20, 2024, 16 pages.

Japanese Office Action for Application No. 2024-557710, dated Apr. 16, 2025, 10 pages including translation.

Japanese Office Action for Application No. 2024-557710, dated Aug. 5, 2025, 6 pages including translation.

Full Text Machine Translation of previously cited reference JP-S61-37171-A, published Feb. 1986, 7 pages.

Japanese Decision of Rejection for Application No. 2024-557710, dated Dec. 2, 2025, 5 pages including translation.

* cited by examiner

OVERMOLDED HEMOLYSIS-REDUCTION ACCESSORIES FOR DIRECT BLOOD DRAW

CROSS REFERENCE TO RELATED APPLICATION

This application claims the benefit of priority under 35 U.S.C. § 119 to U.S. Provisional Patent Application Ser. No. 63/326,705, entitled "OVERMOLDED HEMOLYSIS-REDUCTION ACCESSORIES FOR DIRECT BLOOD DRAW", filed on Apr. 1, 2022, the entire contents of which is incorporated herein by reference.

TECHNICAL FIELD

The present disclosure generally relates to blood draw and administration of parenteral fluids to a patient, and particularly to systems and methods to reduce hemolysis in PIVC blood draw using an overmolded flow restriction device.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter (PIVC). As its name implies, the over-the-needle catheter may be mounted over an introducer needle having a sharp distal tip. A catheter assembly may include a catheter hub, the catheter extending distally from the catheter hub, and the introducer needle extending through the catheter. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

For blood withdrawal or collecting a blood sample from a patient, a blood collection container may be used. The blood collection container may include a syringe. Alternatively, the blood collection container may include a test tube with a rubber stopper at one end. In some instances, the test tube has had all or a portion of air removed from the test tube so pressure within the test tube is lower than ambient pressure. Such a blood collection container is often referred to as an internal vacuum or a vacuum tube. A commonly used blood collection container is a VACUTAINER® blood collection tube, available from Becton Dickinson & Company.

The blood collection container may be coupled to the catheter. When the blood collection container is coupled to the catheter, a pressure in the vein is higher than a pressure in the blood collection container, which pushes blood into the blood collection container, thus filling the blood collection container with blood. A vacuum within the blood collection container decreases as the blood collection container fills, until the pressure in the blood collection container equalizes with the pressure in the vein, and the flow of blood stops.

Unfortunately, as blood is drawn into the blood collection container, red blood cells are in a high shear stress state and susceptible to hemolysis due to a high initial pressure differential between the vein and the blood collection container. Hemolysis may result in rejection and discard of a blood sample. The high initial pressure differential can also result in catheter tip collapse, vein collapse, or other complications that prevent or restrict blood from filling the blood collection container. Furthermore, blood spillage during and/or after blood draw commonly occurs.

The description provided in the background section should not be assumed to be prior art merely because it is mentioned in or associated with the background section. The background section may include information that describes one or more aspects of the subject technology.

SUMMARY

The present disclosure provides a flow restriction device, comprising: a male luer connector portion defining a first lumen; a female luer connector portion defining a second lumen; a tube defining a third lumen, wherein the third lumen is in fluid communication with the first lumen and the second lumen, and the third lumen having a diameter less than 0.025 inches; and an overmolded body portion formed around the tube.

In some instances, the present disclosure provides a method of manufacturing a flow restriction device: providing a tube, wherein the tube defines a lumen having a diameter less than 0.025 inches; and molding an overmolded body portion over the tube In some aspects, the present disclosure provides a peripheral intravenous catheter assembly configured to limit hemolysis during drawing of blood from a patient, comprising: a catheter hub having a proximal end and a distal end; a fluid collection device; and a flow restriction device, comprising: a male luer connector portion defining a first lumen, wherein the male luer connector portion is coupled to the catheter hub; a female luer connector portion defining a second lumen in fluid communication with the fluid collection device; a tube defining a third lumen, wherein the third lumen is in fluid communication with the first lumen and the second lumen, and the third lumen having a diameter less than 0.025 inches; and an overmolded body portion formed around the tube.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
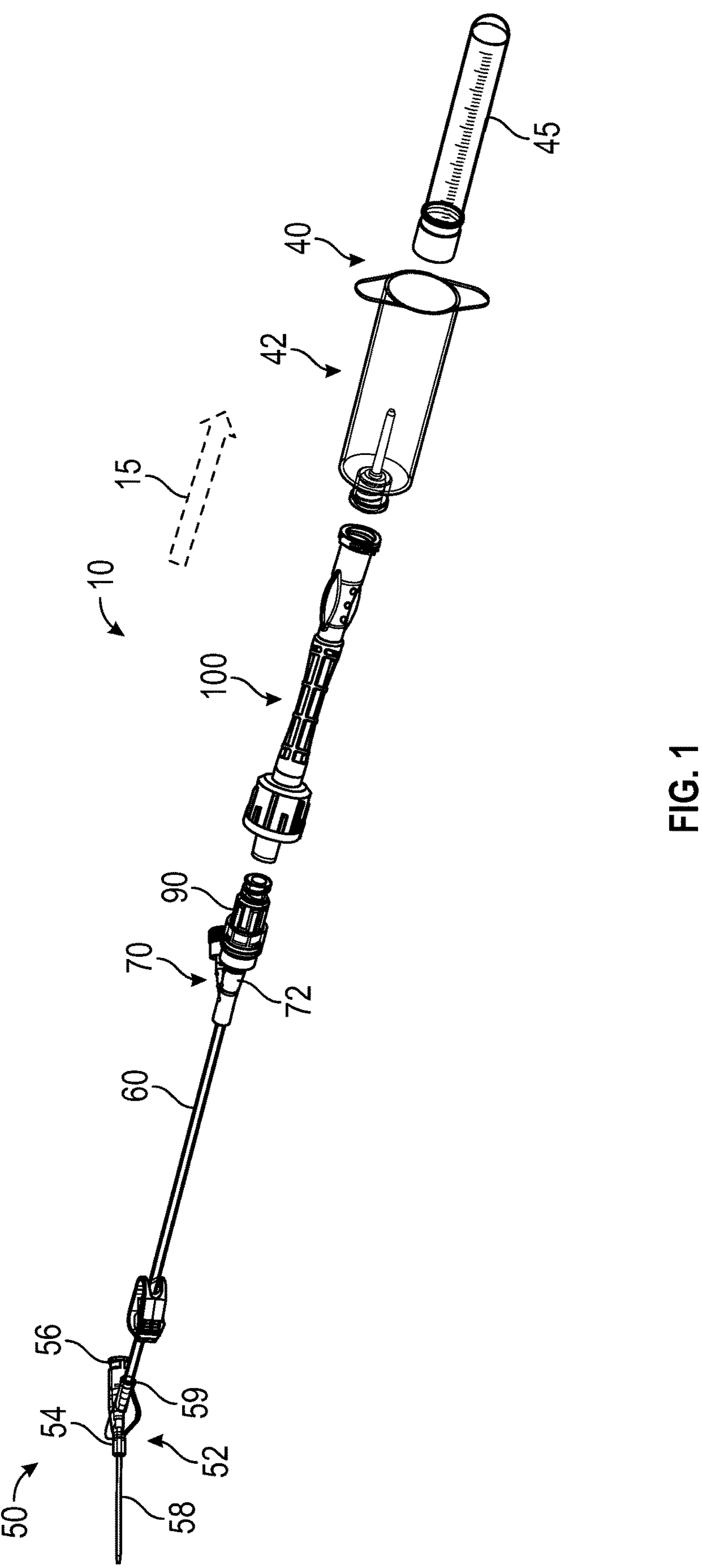
FIG. 1 illustrates a vascular access device including a peripheral intravenous catheter (PIVC) assembly that includes a flow restriction device, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Blood draw via a vascular access device has drawn increasing attention attributed to minimized needle sticks and improved operation efficiency as compared with traditional blood draw methods with venipuncture. Current blood draw using a peripheral intravenous catheter (PIVC) has seen some challenges, one of the most critical is hemolysis related blood quality. In particular, with currently existing PIVC products in the market, along with the standard connection (such as a short extension set and a needleless connector), and blood collection devices (such as a Vacutainer), the shear stress exerted onto blood cells tends to be on the verge of hemolyzing.

Various embodiments of the present disclosure are directed to providing systems and methods to address hemolysis in PIVC blood draw with a hemolysis reduction accessory (also referred to herein as a flow restriction device) which is pre-attached to the PIVC and serves as a flow restrictor to reduce risk of hemolysis. The hemolysis-reduction accessory is advantageously compatible with PIVC placement and does not necessitate change to any of the existing operations. The hemolysis-reduction accessory of the various embodiments described herein is potentially applicable to a wide variety of PIVC products, and compatible with existing blood collection devices and infusion disposables.

Various embodiments of the present disclosure focus on effective flow restriction with the add-on hemolysis-reduction accessory (also referred to herein as a flow restriction device) that regulates the overall flow rate of the entire fluid path as blood cells travel through. The flow restriction device can be either assembled with the PIVC or co-packaged with the PIVC. The clinician may connect a blood collection device to the port of the accessory and can then draw blood to the intended volume. After blood draw, the clinician may disconnect and discard the flow restriction device and the blood collection device together. As such, this flow restriction device can be either for single blood draw or stay inline throughout indwell.

The flow restriction devices and associated blood collection systems of the various embodiments described herein additionally provide further advantages over currently existing blood collection systems. For example, add-on flow restriction devices described herein allow for hemolysis-reduction function to be integrated for PIVC blood draw. Further, the flow restriction devices described herein are compatible with PIVC placement and allow for seamless blood draw at insertion. Additionally, since the flow restriction devices are an add-on which can be easily incorporated without any changes to existing PIVC, there is minimal impact to clinical setting and operations.

FIG. 1 illustrates a vascular access device 10 including a peripheral intravenous catheter (PIVC) assembly 50 that includes a flow restriction device 100, in accordance with some embodiments of the present disclosure. The flow restriction device 100 may be configured to reduce a likelihood of hemolysis during blood collection using the vascular access device 10. In some embodiments, the vascular access device 10 may include a catheter assembly 50. The catheter assembly 50 may include a catheter hub 52, which may include a distal end 54, a proximal end 56, and a lumen extending through the distal end and the proximal end. The catheter assembly 50 may further include a catheter 58, which may be secured within the catheter hub 52 and may extend distally from the distal end 54 of the catheter hub 52. In some embodiments, the catheter assembly 50 may be a peripheral intravenous catheter (PIVC).

In some embodiments, the catheter assembly 50 may include or correspond to any suitable catheter assembly 50. In some embodiments, the catheter assembly 50 may be integrated and include an extension tube 60, which may extend from and be integrated with a side port 59 of the catheter hub 52. A non-limiting example of an integrated catheter assembly is the BD NEXIVA™ Closed IV Catheter system, available from Becton Dickinson and Company. In some embodiments, a proximal end of the extension tube 60 may be coupled to an adapter, such as, for example, a Y-adapter 70. In some embodiments, the flow restriction device 100 may be fluidly coupled to the Y-adapter 70.

In some embodiments, the catheter assembly 50 may be non-integrated and may not include the extension tube 60. In these and other embodiments, the flow restriction device 100 may be configured to couple to the proximal end 56 of the catheter hub 52 or another suitable portion of the catheter assembly 50. In some embodiments, the flow restriction device 100 may be coupled directly to the catheter assembly 50, eliminating the extension tube 60 and providing a compact catheter system.

Figure 2:
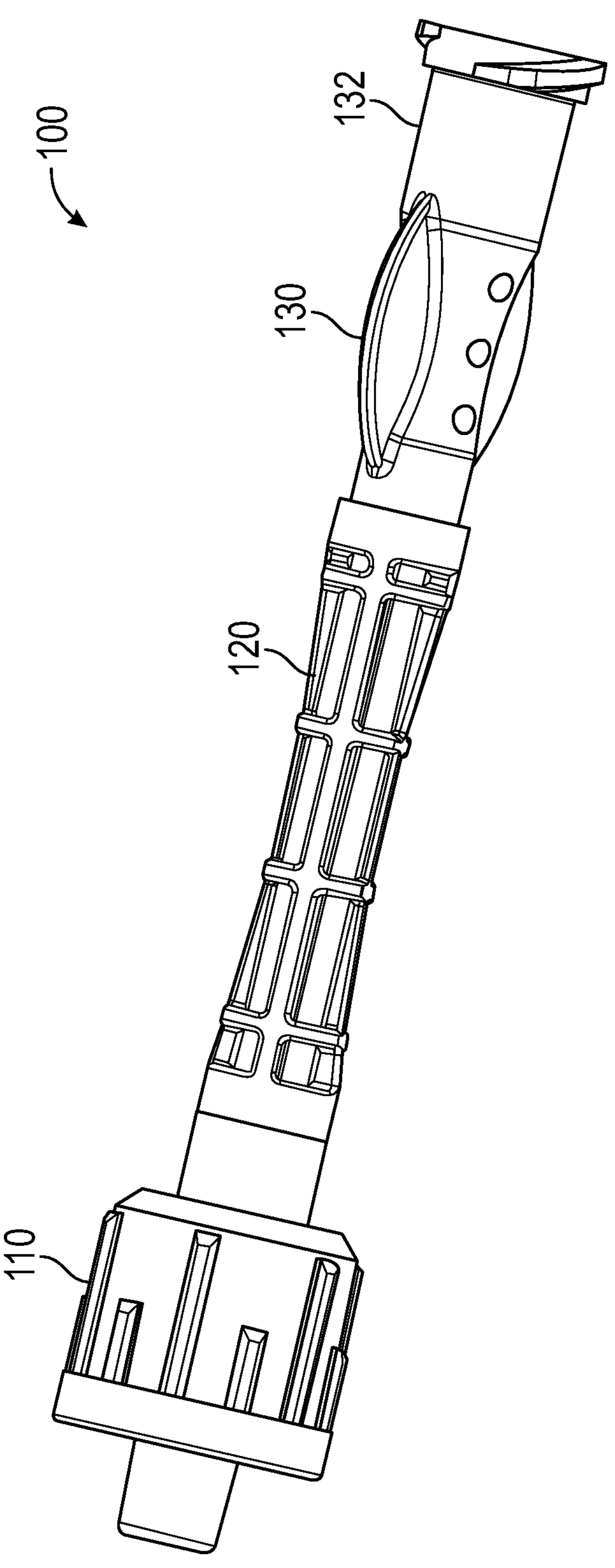
FIG. 2 illustrates a perspective view of the flow restriction device, in accordance with some embodiments of the present disclosure.
Figure 3:
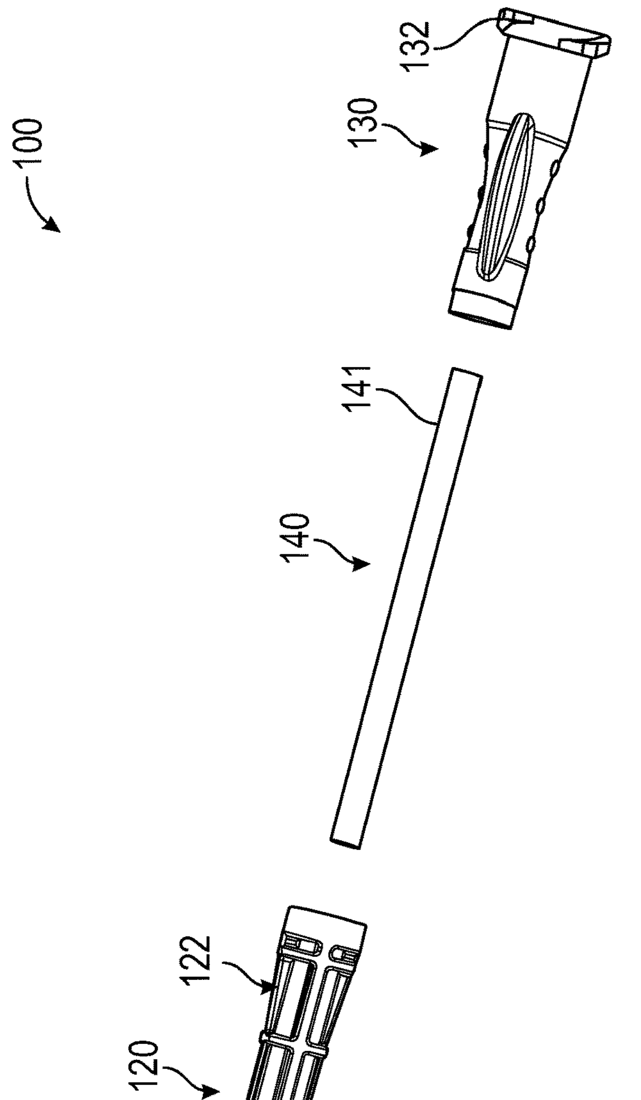
FIG. 3 illustrates an exploded perspective view of the flow restriction device of FIG. 2, in accordance with some embodiments of the present disclosure.
Figure 3:
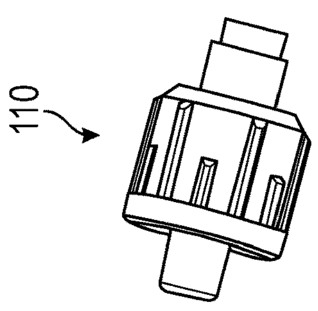
Figure 4:
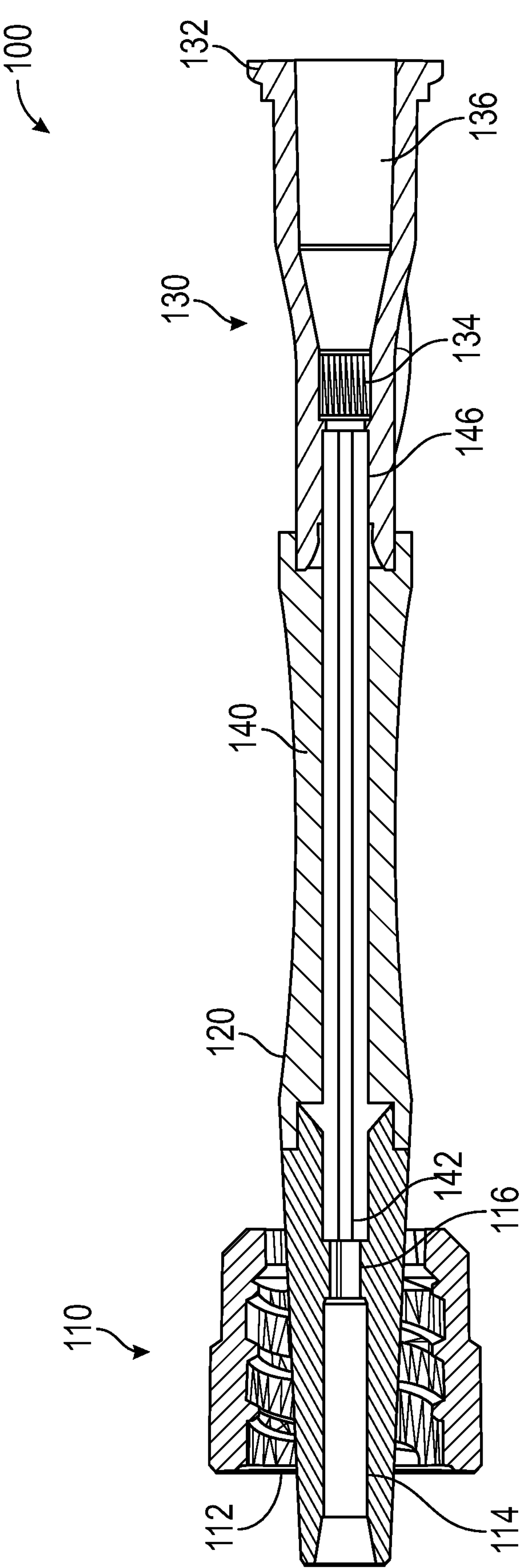
FIG. 4 illustrates a cross-sectional view of the flow restriction device of FIG. 2, in accordance with some embodiments of the present disclosure.

FIG. 2A illustrates a perspective view of the flow restriction device 100, in accordance with some embodiments of the present disclosure. FIG. 3 illustrates an exploded perspective view of the flow restriction device 100 of FIG. 2, in accordance with some embodiments of the present disclosure. FIG. 4 illustrates a cross-sectional view of the flow restriction device 100 of FIG. 2, in accordance with some embodiments of the present disclosure.

As illustrated in FIGS. 2-4, with continued reference to FIG. 1, in some embodiments, the flow restriction device 100 may include a male luer connector portion 110 configured to couple to the catheter assembly 50. The male luer connector portion 110 may have an internal surface 112 defining a lumen 114 of the male luer connector portion 110. In some embodiments, the flow restriction device 100 may further include a female luer connector portion 130 disposed proximally to the male luer connector portion 110. The female luer connector portion 130 may be configured to couple to fluid collection device 40 (e.g., a blood collection device). For example, the female luer connector portion 130 may be integrated with the blood collection device 40 or monolithically formed with the blood collection device 40 as a single unit or piece. As another example, the female luer connector portion 130 may be in the form of a female luer connector or another suitable connector, which may be coupled with a male luer portion of the blood collection device 40. The female luer connector portion 130 may include an internal surface 132 defining a lumen 136 extending therethrough for coupling to the male luer portion of the blood collection device 40. The lumen 136 of the female luer connector portion 130 may be fluidly connected to the lumen 114 of the male luer connector portion 110 via a tube 140 of the flow restriction device 100, as shall be described below.

In the depicted example, the flow restriction device 100 includes a tube 140 extending longitudinally therethrough and fluidly communicated with the lumens 114 and 136 of the male luer portion 110 and the female luer portion 130, respectively. The tube 140 may define a micro-channel 142 along which a fluid flows from the male luer connector portion 110 into the fluid collection device 40 via the female luer connector portion 130. As depicted, the tube 140 may fluidly communicate the catheter assembly 50 with the fluid collection device 40 via the flow restriction device 100. For example, in some embodiments, a leg 72 of the Y-adapter 70 may be coupled to the flow restriction device 100. The leg 72 of Y-adapter 70 may include a lumen into which the distal end of the male luer connector portion 110 may be coupled. The Y-adapter 70 may fluidly communicate the flow restriction device 100 via a connector 90, which is depicted as a needleless connector, and the tube 140 with the catheter assembly 50, for example, via the extension tubing 60. Accordingly, the micro-channel 142 may define a fluid pathway with a reduced, small, or micro-sized diameter (as discussed below) through which fluid entering the flow restriction device 100 from the catheter assembly 50, may flow through the flow restriction device 100 for collection in the fluid collection device 40. For example, where blood is being withdrawn or collected from a patient, the medical fluid may be blood, and the fluid collection device 40 may be a blood collection device. In some embodiments, the blood collection device may be a luer lock access device (LLAD). Accordingly, during blood collection or withdrawal from the patients, the blood sample may flow from the distal end of the male luer connector portion 110 into the LLAD 40 via the flowpath or micro-channel 142 defined by the tube 140.

In some embodiments, micro-channel 142 defined by the tube 140 may be an elongate, thin channel having a small, reduced, or micro-sized diameter. For example, in some embodiments, the tube 140 which defines the flowpath or micro-channel along which fluid may flow from the male luer connector portion 110 into the fluid collection device 40, may have a diameter in the range of a twenty thousandth to twenty-five thousandth of an inch. However, the various embodiments of the present disclosure are not limited to the aforementioned configuration. In some embodiments, the length of the micro-channel 142 may range from 1 to 1.3 inches. Accordingly, during blood collection or withdrawal from the patient, the blood 15 may flow into the blood collection device 40 via the flowpath or micro-channel defined by the micro-channel 142 having minimal diameter. The flow restriction device 100 of the various embodiments described herein is advantageous over currently existing blood collection systems. For example, during blood draw with currently existing blood draw devices, blood cells may experience wall shear stress as they flow from the distal end to the proximal end of the blood collection systems. Wall shear stress on blood cells is considered a major source of mechanical damage to blood cells causing hemolysis of the blood cells. The micro-channel 142 having minimal diameter may facilitate increased flow resistance within the vascular access system to distribute the pressure differential and reduce shear stress experienced by the red blood cells of the blood 15. For example, the minimized diameter of the micro-channel 142 may provide increased resistance to flow of the blood 15 and thereby decrease blood flow rate within the flow resistance device 100. Since the decreased blood flow rate causes a reduction in shear stress experienced by the red blood cells of the blood 15, a risk of hemolysis during blood collection may advantageously be reduced. Further, the geometry of the micro-channel 142 can reduce the amount of blood wasted by currently existing blood collection systems.

In accordance with various embodiments of the present disclosure, the flow restriction device 100 may further include a body portion 120 overmolded the tube 140 and extending between the male luer 110 portion and the female luer portion 130

According to various embodiments of the present disclosure, an outer surface 122 of the body portion 120 may include a plurality of laterally extending ribs disposed about and surrounding a longitudinal axis of the body portion 120. As depicted, the plurality of laterally extending ribs may be spaced apart from each other along the longitudinal axis X between the female luer connector portion 130 and the male luer connector portion 110. In some embodiments, the outer surface 122 may further include at least one longitudinally extending rib disposed along the longitudinal axis and extending from the male luer connector portion 110 to the female luer connector portion 130. In some embodiments, as illustrated in FIG. 2, the body portion 120 may include a pair of longitudinally extending ribs disposed at opposing sides of the body portion 120. As depicted, the longitudinally extending rib may be disposed transverse to and may interconnect each of the laterally extending ribs. The plurality of laterally extending ribs and the one or more longitudinally extending ribs may thus form a grid or matrix shape surrounding the body portion 120.

The grid or matrix shape surrounding the body portion 120 may advantageously provide additional or enhanced structural integrity or rigidity as compared with currently existing connectors for blood collection systems. For example, in some embodiments, the grid or matrix shape of the laterally extending ribs and the longitudinally extending ribs surrounding the body portion 120 may provide increased rigidity between the male luer connector portion 110 and the female luer connector portion 130 of the flow restriction device 100, thereby making the flow restriction device 100 less susceptible to bending or twisting forces. The aforementioned configuration is advantageous in that the enhanced rigidity of the flow restriction device 100 makes it less flexible thereby decreasing the possibility of blood spillage due to accidental or inadvertent bending or twisting of the flow control device 100. The aforementioned configuration of the flow restriction device with the laterally extending ribs and the longitudinally extending ribs surrounding the body portion 120 may further be advantageous in providing a surface on the body portion that is easier to grip than would a more uniform surface of the body portion 120 be to grip.

As described herein, the body portion 120 is overmolded over the tube 140 to provide a gripping surface for a clinician. In some embodiments, the body portion 120 can also extend over portions of the male luer connector portion 110 and/or the female luer connector portion 130. Advantageously, by overmolding the body portion 120, the flow control device 100 can provide a gripping surface for the clinician while reducing manufacturing complexity of the flow control device 100. For example, the body portion 120 can be molded directly on top of the tube 140 to create a single piece include the tube 140 and the body portion 120. Advantageously, the body portion 120 can define a simplified profile to simplify the overmolding process. In some embodiments, the body portion 120 can utilize a polymeric or elastomeric material. The aforementioned configuration in which the flow restriction device 100 is formed with an overmolded body simplifies the manufacturing process while allowing for robust construction of the flow restriction device 100.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A flow restriction device, comprising: a male luer connector portion defining a first lumen; a female luer connector portion defining a second lumen; a tube defining a third lumen, wherein the third lumen is in fluid communication with the first lumen and the second lumen, and the third lumen having a diameter less than 0.025 inches; and an overmolded body portion formed around the tube.

Clause 2. The flow restriction device of Clause 1, wherein the third lumen has a length of about 1 inch to about 1.3 inches.

Clause 3. The flow restriction device of Clause 1, wherein the third lumen is configured to increase flow resistance through the third lumen to minimize shear stress experienced by the fluid flow.

Clause 4. The flow restriction device of Clause 1, wherein the overmolded body portion extends over a portion of the male luer connector portion.

Clause 5. The flow restriction device of Clause 1, wherein the overmolded body portion extends over a portion of the female luer connector portion.

Clause 6. The flow restriction device of Clause 1, wherein the overmolded body portion comprises a first material and the tube comprises a second material, and the first material is different than the second material.

Clause 7. The flow restriction device of Clause 6, wherein the first material comprises an elastomeric or polymeric material.

Clause 8. The flow restriction device of Clause 1, wherein an outer surface of the overmolded body portion comprises a plurality of laterally extending ribs disposed about and surrounding a longitudinal axis of the overmolded body portion, the plurality of ribs being spaced apart from each other along the longitudinal axis between the female luer connector portion and the male luer connector portion.

Clause 9. The flow restriction device of Clause 8, wherein the outer surface of the overmolded body portion further comprises at least one longitudinally extending rib disposed along the longitudinal axis and extending from the male luer connector portion to the female luer connector portion.

Clause 10. A method of manufacturing a flow restriction device:

providing a tube, wherein the tube defines a lumen having a diameter less than 0.025 inches; and molding an overmolded body portion over the tube.

Clause 11. The method of Clause 10, wherein the overmolded body portion comprises a first material and the tube comprises a second material, and the first material is different than the second material.

Clause 12. The method of Clause 11, wherein the first material comprises an elastomeric or polymeric material.

Clause 13. A peripheral intravenous catheter assembly configured to limit hemolysis during drawing of blood from a patient, comprising: a catheter hub having a proximal end and a distal end; a fluid collection device; and a flow restriction device, comprising: a male luer connector portion defining a first lumen, wherein the male luer connector portion is coupled to the catheter hub; a female luer connector portion defining a second lumen in fluid communication with the fluid collection device; a tube defining a third lumen, wherein the third lumen is in fluid communication with the first lumen and the second lumen, and the third lumen having a diameter less than 0.025 inches; and an overmolded body portion formed around the tube.

Clause 14. The peripheral intravenous catheter assembly of Clause 13, wherein the third lumen has a length of about 1 inch to about 1.3 inches.

Clause 15. The peripheral intravenous catheter assembly of Clause 13, wherein the third lumen is configured to increase flow resistance through the third lumen to minimize shear stress experienced by the fluid flow.

Clause 16. The peripheral intravenous catheter assembly of Clause 13, wherein the overmolded body portion extends over a portion of the male luer connector portion.

Clause 17. The peripheral intravenous catheter assembly of Clause 13, wherein the overmolded body portion extends over a portion of the female luer connector portion.

Clause 18. The peripheral intravenous catheter assembly of Clause 13, wherein the overmolded body portion comprises a first material and the tube comprises a second material, and the first material is different than the second material.

Clause 19. The peripheral intravenous catheter assembly of Clause 18 wherein the first material comprises an elastomeric or polymeric material.

Clause 20. The peripheral intravenous catheter assembly of Clause 13, wherein an outer surface of the overmolded body portion comprises a plurality of laterally extending ribs disposed about and surrounding a longitudinal axis of the overmolded body portion, the plurality of ribs being spaced apart from each other along the longitudinal axis between the female luer connector portion and the male luer connector portion.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A flow restriction device, comprising:

a male luer connector portion defining a first lumen;

a female luer connector portion defining a second lumen;

a tube partially disposed within each of the first lumen and the second lumen and defining a third lumen, in fluid communication with the first lumen and the second lumen, wherein the third lumen comprises a diameter less than 0.025 inches; and an overmolded body portion formed around the tube, wherein the overmolded body portion extends over a portion of the male luer connector portion and a portion of the female luer connector portion.

2. The flow restriction device of claim 1, wherein the third lumen comprises a length of 1 inch to 1.3 inches.

3. The flow restriction device of claim 1, wherein the third lumen is configured to increase flow resistance through the third lumen to minimize shear stress experienced by the fluid flow.

4. The flow restriction device of claim 1, wherein the overmolded body portion comprises a first material and the tube comprises a second material, and the first material is different than the second material.

5. The flow restriction device of claim 4, wherein the first material comprises an elastomeric or polymeric material.

6. The flow restriction device of claim 1, wherein an outer surface of the overmolded body portion comprises a plurality of laterally extending ribs disposed about and surrounding a longitudinal axis of the overmolded body portion, the plurality of ribs being spaced apart from each other along the longitudinal axis between the female luer connector portion and the male luer connector portion.

7. The flow restriction device of claim 6, wherein the outer surface of the overmolded body portion further comprises at least one longitudinally extending rib disposed along the longitudinal axis and extending from the male luer connector portion to the female luer connector portion.

8. A peripheral intravenous catheter assembly configured to limit hemolysis during drawing of blood from a patient, comprising:

a catheter hub comprising a proximal end and a distal end;

a fluid collection device; and a flow restriction device, comprising:

a male luer connector portion defining a first lumen, wherein the male luer connector portion is coupled to the catheter hub;

a female luer connector portion defining a second lumen in fluid communication with the fluid collection device;

a tube partially disposed within each of the first lumen and the second lumen and defining a third lumen, in fluid communication with the first lumen and the second lumen, wherein the third lumen comprises a diameter less than 0.025 inches; and an overmolded body portion formed around the tube, wherein the overmolded body portion extends over a portion of the male luer connector portion and a portion of the female luer connector portion.

9. The peripheral intravenous catheter assembly of claim 8, wherein the third lumen comprises a length of 1 inch to 1.3 inches.

10. The peripheral intravenous catheter assembly of claim 8, wherein the third lumen is configured to increase flow resistance through the third lumen to minimize shear stress experienced by the fluid flow.

11. The peripheral intravenous catheter assembly of claim 8, wherein the overmolded body portion comprises a first material and the tube comprises a second material, and the first material is different than the second material.

12. The peripheral intravenous catheter assembly of claim 11 wherein the first material comprises an elastomeric or polymeric material.

13. The peripheral intravenous catheter assembly of claim 8, wherein an outer surface of the overmolded body portion comprises a plurality of laterally extending ribs disposed about and surrounding a longitudinal axis of the overmolded body portion, the plurality of ribs being spaced apart from each other along the longitudinal axis between the female luer connector portion and the male luer connector portion.

14. The flow restriction device of claim 1, wherein the first lumen comprises a first diameter, the second lumen comprises a second diameter, and the diameter of the third lumen is less than the first diameter and the second diameter.

15. The peripheral intravenous catheter assembly of claim 8, wherein the first lumen comprises a first diameter, the second lumen comprises a second diameter, and the diameter of the third lumen is less than the first diameter and the second diameter.

* * * * *